US012648760B2

(12) United States Patent
Li et al.

(10) Patent No.: US 12,648,760 B2
(45) Date of Patent: Jun. 9, 2026

(54) ULTRASONIC IMAGING SYSTEM AND ULTRASONIC IMAGING METHOD

(71) Applicant: SHENZHEN MINDRAY BIO-MEDICAL ELECTRONICS CO., LTD., Shenzhen (CN)

(72) Inventors: Shuangshuang Li, Shenzhen (CN); Xiao Chen, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 199 days.

(21) Appl. No.: 18/202,148

(22) Filed: May 25, 2023

(65) Prior Publication Data

US 2023/0380810 A1     Nov. 30, 2023

(30) Foreign Application Priority Data

May 27, 2022     (CN) .......................... 202210594319.6

(51) Int. Cl.
*A61B 8/00*             (2006.01)

(52) U.S. Cl.
CPC .............. *A61B 8/485* (2013.01); *A61B 8/463* (2013.01); *A61B 8/54* (2013.01)

(58) Field of Classification Search
CPC ...................................................... A61B 8/485
See application file for complete search history.

(56) References Cited

U.S. PATENT DOCUMENTS

2023/0026896 A1 *    1/2023   Zhang ................... A61B 8/485

FOREIGN PATENT DOCUMENTS

EP           3231369 A1 *  11/2015

* cited by examiner

*Primary Examiner* — Joel Lamprecht
(74) *Attorney, Agent, or Firm* — Sheppard Mullin Richter & Hampton LLP

(57)          ABSTRACT

Disclosed are an ultrasonic imaging system and an ultrasonic imaging method, in which echo signals of ultrasonic waves of a region of interest are received, shear waves are propagated within the region of interest, the ultrasonic waves are used for detecting the shear waves; an elasticity result of the region of interest is calculated based on the echo signals of ultrasonic waves; a viscosity parameter of the region of interest is calculated based on the echo signals of ultrasonic waves; and the elasticity result is performed with quality control at least based on the viscosity parameter. The present disclosure provides a scheme of quality control prompt for the reliability of the elasticity result by means of tissue viscosity characteristics.

8 Claims, 5 Drawing Sheets

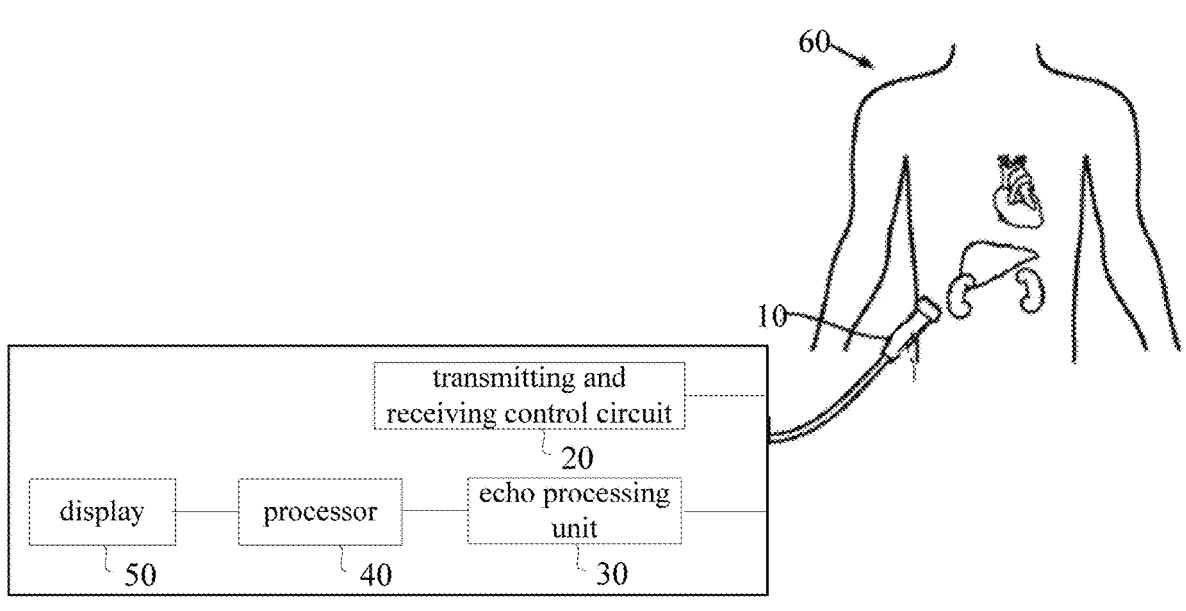
FIG. 1
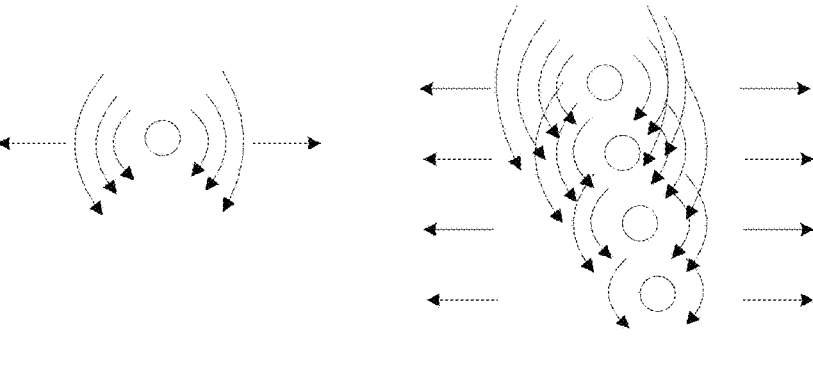
FIG. 2(a)                       FIG. 2(b)

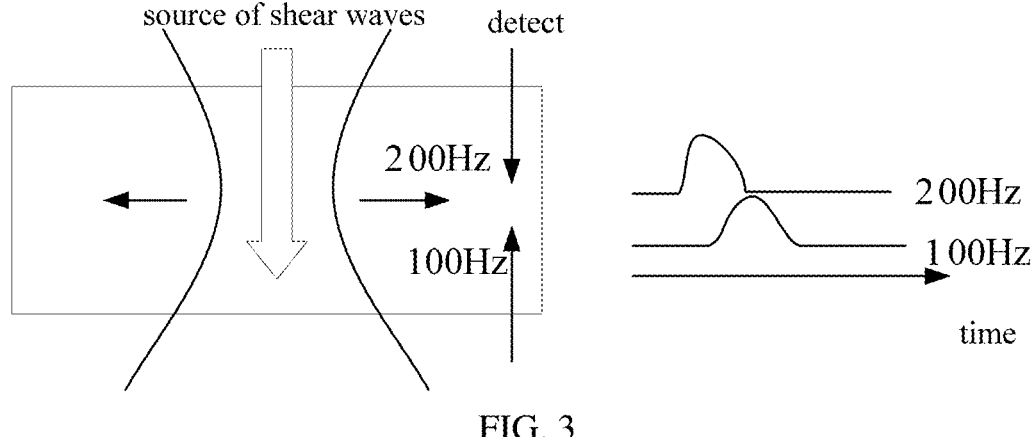
FIG. 3
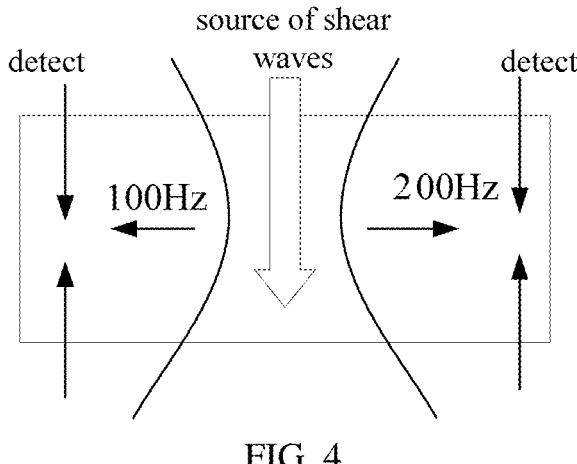
FIG. 4
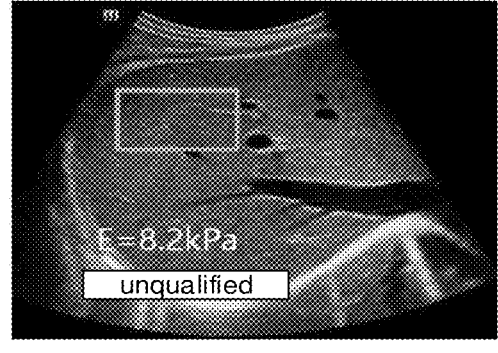
FIG. 5
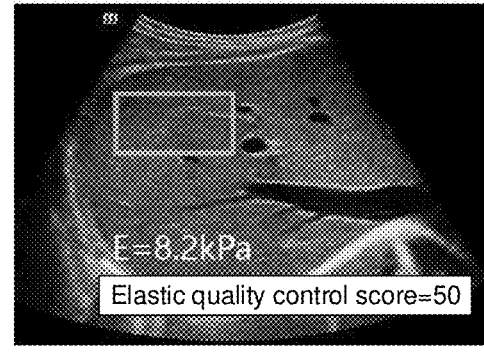
FIG. 6

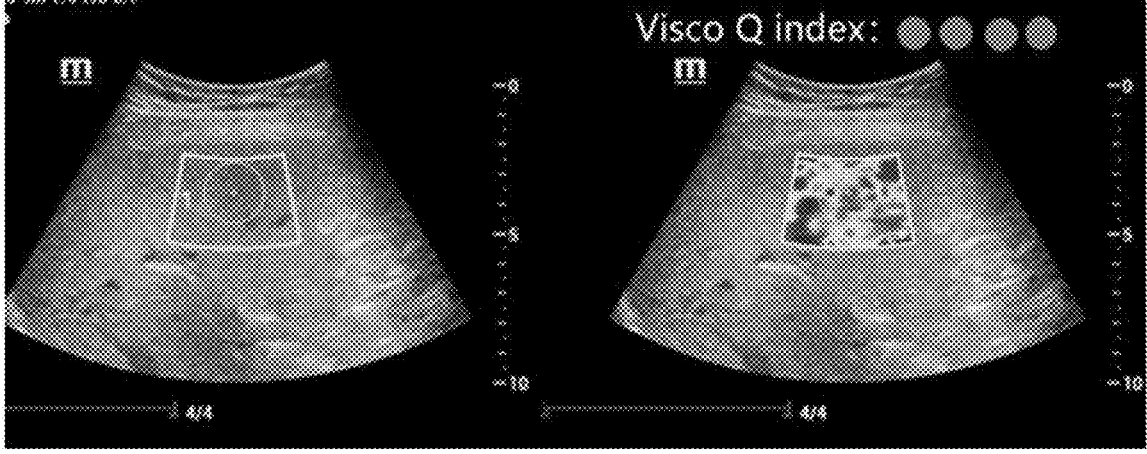

FIG. 10

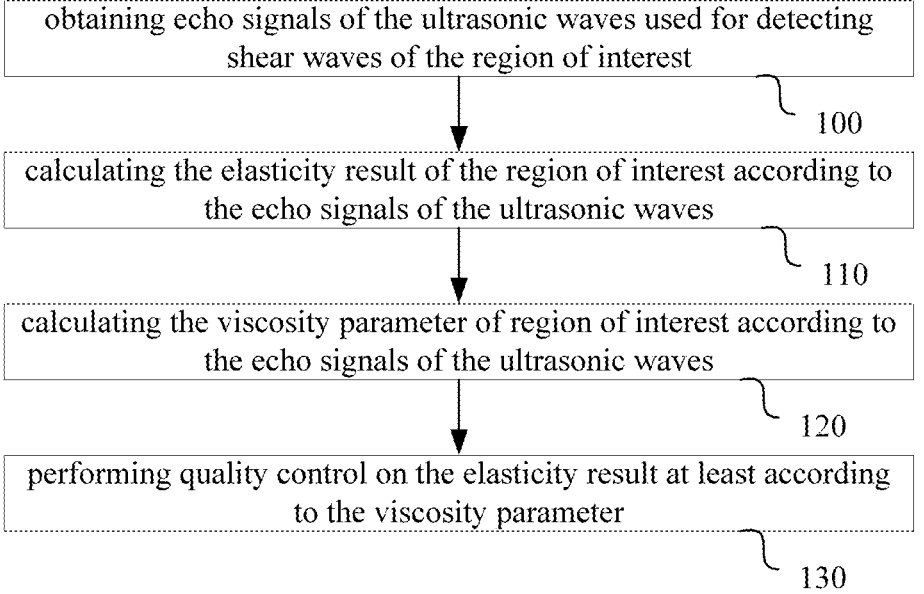

obtaining echo signals of the ultrasonic waves used for detecting shear waves of the region of interest

⌐ 100 calculating the elasticity result of the region of interest according to the echo signals of the ultrasonic waves

⌐ 110 calculating the viscosity parameter of region of interest according to the echo signals of the ultrasonic waves

⌐ 120 performing quality control on the elasticity result at least according to the viscosity parameter

ULTRASONIC IMAGING SYSTEM AND ULTRASONIC IMAGING METHOD

CROSS-REFERENCE TO RELATED APPLICATIONS

This application is based on and claims priority to and benefits of Chinese Patent Application No. 202210594319.6, filed on May 27, 2022. The entire content of the above-referenced application is incorporated herein by reference.

TECHNICAL FIELD

The present disclosure relates to ultrasonic imaging systems and ultrasonic imaging methods.

BACKGROUND

Elasticity imaging technology, one of the hot spots in clinical research in recent years, mainly reflects the degree of elasticity or hardness of tissues, and has been increasingly applied in auxiliary detection of tissue cancer lesions, benign and malignant discrimination, prognosis recovery evaluation and other aspects. Specifically, ultrasonic elasticity imaging is performed by extracting hardness related information about tissues; and after years of development, ultrasonic elasticity imaging techniques have been gradually mature, and has been widely used in clinical research and auxiliary diagnosis of various parts of human body (such as liver, breast, thyroid, musculoskeletal, vascular, prostate, cervix, etc.) in recent years. It can reflect qualitatively the soft and hard difference of the lesion relative to the surrounding tissue, or reflect quantitatively the physical parameters related to the hardness of the target tissue, such as Young's modulus, shear modulus, etc., which is welcomed widely by doctors.

Common ultrasonic elasticity imaging techniques include strain elasticity imaging, transient elasticity imaging and shear-wave elasticity imaging which is especially the latest one. Shear wave elasticity imaging is performed by transmitting special pulses into tissues to produce acoustic radiation force to generate the propagation of shear wave, then detecting and recording the propagation process of shear wave by ultrasonic wave, further calculating the propagation velocity of shear wave, and finally obtaining elasticity modulus parameters reflecting the hardness of the tissues to achieve quantitative elasticity imaging. This technique has greatly expanded the clinical application field of elasticity imaging, attracting great research interest.

Although ultrasonic elasticity imaging technology has the above advantages and applications, if elasticity results obtained by ultrasonic elasticity imaging technology are unreliable, it will bring adverse effects on the diagnosis of doctors. Therefore, it is necessary to conduct quality control on the elasticity results obtained by ultrasonic elasticity imaging technology.

SUMMARY

The present disclosure provides ultrasonic imaging systems and ultrasonic imaging methods, which are described in detail below, to solve at least one of the above problems.

According to a first aspect, an ultrasonic imaging system provided in an embodiment may include:

an ultrasonic probe for transmitting ultrasonic waves and receiving echo signals of the ultrasonic waves;

a transmitting and receiving control circuit for controlling the ultrasonic probe to perform transmission of the ultrasonic waves and reception of the echo signals of the ultrasonic waves;

a processor and a display;

the processor being configured to:

control the ultrasonic probe via the transmitting and receiving control circuit to transmit first ultrasonic waves to a target tissue and receive echo signals of the first ultrasonic waves, and generate an ultrasonic image of the target tissue according to the echo signals of the first ultrasonic waves;

control the display to display the ultrasonic image, and obtain a region of interest on the ultrasonic image;

control the ultrasonic probe via the transmitting and receiving control circuit to transmit second ultrasonic waves to the region of interest and receive echo signals of the second ultrasonic waves, wherein the region of interest has propagation of shear waves therein, and the second ultrasonic waves are used for detecting the shear waves;

calculate an elasticity result and a viscosity parameter of the region of interest according to the echo signals of the second ultrasonic waves; and perform quality control on the elasticity result at least according to the viscosity parameter.

In an embodiment, the processor calculating the viscosity parameter of the region of interest according to the echo signals of the second ultrasonic waves may comprise:

obtaining phase velocities of shear waves of at least two frequencies according to the echo signals of the second ultrasonic waves; and calculating a discrepancy in the phase velocities of shear waves of at least two frequencies as the viscosity parameter.

In an embodiment, said discrepancy in the phase velocities of shear waves of at least two frequencies comprises a difference or a ratio of the phase velocities of shear waves of at least two frequencies.

In an embodiment, the processor calculating the viscosity parameter of the region of interest according to the echo signals of the second ultrasonic waves comprises:

obtaining phase velocities of shear waves of at least two frequencies according to echo signals of the second ultrasonic waves; and calculating frequency dispersion slope value as the viscosity parameter according to the phase velocities of shear waves of at least two frequencies and corresponding frequencies.

In an embodiment, the processor calculating the viscosity parameter of the region of interest according to the echo signals of the second ultrasonic waves comprises:

obtaining a phase velocity of shear waves of at least one frequency according to the echo signals of the second ultrasonic waves; and calculating a viscosity as the viscosity parameter according to the phase velocity of shear waves of at least one frequency and corresponding frequencies.

In an embodiment, the processor performing quality control on the elasticity result at least according to the viscosity parameter comprises:

comparing the viscosity parameter with one or more thresholds to evaluate reliability of the elasticity result to generate a corresponding prompt; and controlling the display to display the prompt.

In an embodiment, the processor performing quality control on the elasticity result at least according to the viscosity parameter comprises:

generating an elasticity quality control score at least according to the viscosity parameter; and controlling the display to display the elasticity quality control score.

In an embodiment, the processor performing quality control on the elasticity result at least according to the viscosity parameter comprises:

generating an elasticity quality control distribution diagram at least according to the viscosity parameter; and controlling the display to display the elasticity quality control distribution diagram.

In an embodiment, the processor performing quality control on the elasticity result at least according to the viscosity parameter comprises:

emptying a region in an elasticity distribution diagram where quality control fails to meet a predetermined requirement at least according to the viscosity parameter, the elasticity distribution diagram being generated according to the elasticity result.

According to a second aspect, an ultrasonic imaging system provided in an embodiment may include:

an ultrasonic probe for transmitting ultrasonic waves and receiving echo signals of the ultrasonic waves;

a transmitting and receiving control circuit for controlling the ultrasonic probe to perform transmission of the ultrasonic waves and reception of the echo signals of the ultrasonic waves;

a processor and a display;

the processor being configured to:

receive echo signals of the ultrasonic waves of a region of interest, wherein the region of interest has propagation of shear waves therein, and the ultrasonic waves are used for detecting the shear waves;

calculating an elasticity result and a viscosity parameter of the region of interest according to the echo signals of the ultrasonic waves; and perform quality control on the elasticity result at least according to the viscosity parameter.

In an embodiment, the processor calculating the viscosity parameter of the region of interest according to the echo signals of the ultrasonic waves comprises:

obtaining phase velocities of shear waves of at least two frequencies according to the echo signals of the ultrasonic waves, and calculating a discrepancy in the phase velocities of shear waves of at least two frequencies as the viscosity parameter; and/or, obtaining phase velocities of shear waves of at least two frequencies according to the echo signals of the ultrasonic waves, and calculating a frequency dispersion slope value as the viscosity parameter according to the phase velocities of shear waves of at least two frequencies and corresponding frequencies; and/or, obtaining a phase velocity of shear waves of at least one frequency according to the echo signals of the ultrasonic waves, and calculating a viscosity as the viscosity parameter according to the phase velocity of shear waves of at least one frequency and corresponding frequency.

In an embodiment, the processor performing quality control on the elasticity result at least according to the viscosity parameter comprises:

comparing the viscosity parameter with one or more thresholds to evaluate reliability of the elasticity result to generate a corresponding prompt, and controlling the display to display the prompt;

and/or, generating an elasticity quality control score at least according to the viscosity parameter, and controlling the display to display the elasticity quality control score;

and/or, generating an elasticity quality control distribution diagram at least according to the viscosity parameter, and controlling the display to display the elasticity quality control distribution diagram;

and/or, emptying a region in an elasticity distribution diagram where quality control fails to meet a predetermined requirement at least according to the viscosity parameter, the elasticity distribution diagram being generated according to the elasticity result.

According to a third aspect, an ultrasonic imaging method provided in an embodiment may include:

controlling an ultrasonic probe to transmit first ultrasonic waves to a target tissue and receive echo signals of the first ultrasonic waves;

generating an ultrasonic image of the target tissue according to the echo signals of the first ultrasonic waves;

controlling a display to display the ultrasonic image;

obtaining a region of interest on the ultrasonic image;

controlling the ultrasonic probe to transmit second ultrasonic waves to the region of interest and receive echo signals of the second ultrasonic waves, wherein the region of interest has propagation of shear waves therein, and the second ultrasonic waves are used for detecting the shear waves;

calculating an elasticity result of the region of interest according to the echo signals of the second ultrasonic waves;

calculating a viscosity parameter of the region of interest according to the echo signals of the second ultrasonic waves; and performing quality control on the elasticity result at least according to the viscosity parameter.

In an embodiment, calculating a viscosity parameter of the region of interest according to the echo signals of the second ultrasonic waves comprises:

obtaining phase velocities of shear waves of at least two frequencies according to the echo signals of the second ultrasonic waves; and calculating a discrepancy in the phase velocities of shear waves of at least two frequencies as the viscosity parameter.

In an embodiment, the discrepancy in the phase velocities of shear waves of at least two frequencies comprises a difference or a ratio of the phase velocities of shear waves of at least two frequencies.

In an embodiment, calculating a viscosity parameter of the region of interest according to the echo signals of the second ultrasonic waves comprises:

obtaining phase velocities of shear waves of at least two frequencies according to the echo signals of the second ultrasonic waves; and calculating a frequency dispersion slope value as the viscosity parameter according to the phase velocities of shear waves of at least two frequencies and corresponding frequencies.

In an embodiment, calculating a viscosity parameter of the region of interest according to the echo signals of the second ultrasonic waves comprises:

obtaining a phase velocity of shear waves of at least one frequency according to the echo signals of the second ultrasonic waves; and calculating a viscosity as the viscosity parameter according to the phase velocity of shear waves of at least one frequency and corresponding frequency.

In an embodiment, performing quality control on the elasticity result at least according to the viscosity parameter comprises:

comparing the viscosity parameter with one or more threshold to evaluate reliability of the elasticity result to generate a corresponding prompt; and controlling the display to display the prompt.

In an embodiment, performing quality control on the elasticity result at least according to the viscosity parameter comprises:

generating an elasticity quality control score at least according to the viscosity parameter; and controlling the display to display the elasticity quality control score.

In an embodiment, performing quality control on the elasticity result at least according to the viscosity parameter comprises:

generating an elasticity quality control distribution diagram at least according to the viscosity parameter; and controlling the display to display the elasticity quality control distribution diagram.

In an embodiment, performing quality control on the elasticity result at least according to the viscosity parameter comprises:

emptying a region in an elasticity distribution diagram where quality control fails to meet a predetermined requirement at least according to the viscosity parameter, the elasticity distribution diagram being generated according to the elasticity result.

According to a fourth aspect, an ultrasonic imaging method provided in an embodiment may include:

obtaining echo signals of the ultrasonic waves of a region of interest, the region of interest having propagation of shear waves therein and the ultrasonic waves being used for detecting the shear waves;

calculating an elasticity result of the region of interest according to the echo signals of the ultrasonic waves;

calculating a viscosity parameter of the region of interest according to the echo signals of the ultrasonic waves; and performing quality control on the elasticity result at least according to the viscosity parameter.

In an embodiment, calculating a viscosity parameter of the region of interest according to the echo signals of the ultrasonic waves comprises:

obtaining phase velocities of shear waves of at least two frequencies according to the echo signals of the ultrasonic waves, and calculating a discrepancy in the phase velocities of shear waves of at least two frequencies as the viscosity parameter;

and/or, obtaining phase velocities of shear waves of at least two frequencies according to the echo signals of the ultrasonic waves, and calculating a frequency dispersion slope value as the viscosity parameter according to the phase velocities of shear waves of at least two frequencies and corresponding frequencies;

and/or, obtaining a phase velocity of shear waves of at least one frequency according to the echo signals of the ultrasonic waves, and calculating a viscosity as the viscosity parameter according to the phase velocity of shear waves of at least one frequency and corresponding frequency.

In an embodiment, performing quality control on the elasticity result at least according to the viscosity parameter comprises:

comparing the viscosity parameter with one or more threshold to evaluate reliability of the elasticity result to generate a corresponding prompt, and controlling a display to display the prompt;

and/or, generating an elasticity quality control score at least according to the viscosity parameter, and controlling the display to display the elasticity quality control score;

and/or, generating an elasticity quality control distribution diagram at least according to the viscosity parameter, and controlling the display to display the elasticity quality control distribution diagram;

and/or, emptying a region in an elasticity distribution diagram where quality control fails to meet a predetermined requirement at least according to the viscosity parameter, the elasticity distribution diagram being generated according to the elasticity result.

According to the ultrasonic imaging systems and the ultrasonic imaging methods mentioned in above embodiments, echo signals of the ultrasonic waves of a region of interest is obtained, wherein shear waves are propagated in the region of interest and the ultrasonic waves is used for detecting the shear waves; the elasticity result of the region of interest is calculated based on the echo signals of the ultrasonic waves; the viscosity parameter of the region of interest is calculated based on the echo signals of the ultrasonic waves; and the elasticity result is performed with quality control at least according to the viscosity parameter; in this way, the present disclosure provides a scheme of quality control prompt for the reliability of the elasticity result by means of tissue viscosity characteristics.

BRIEF DESCRIPTION OF THE DRAWINGS

FIG. 1 is a schematically structural diagram of an ultrasonic imaging system according to an embodiment;

FIG. 2($a$) is a schematic diagram of shear waves generated by strong focusing according to an embodiment, FIG. 2($b$) is a schematic diagram of propagation of shear waves started from different locations by focusing on different regions respectively according to an embodiment;

FIG. 3 is a schematic diagram of calculating phase velocities at 100 Hz and 200 Hz according to an embodiment;

FIG. 4 is a schematic diagram of calculating phase velocities at 100 Hz and 200 Hz according to another embodiment;

FIG. 5 is a schematic diagram of performing quality control on the elasticity result based at least on the viscosity parameter according to an embodiment;

FIG. 6 is a schematic diagram of performing quality control on the elasticity result based at least on the viscosity parameter according to another embodiment;

FIG. 10 is a schematic diagram of performing quality control on the elasticity result based at least on the viscosity parameter according to yet still another embodiment; and FIG. 11 is a flowchart of an ultrasonic imaging method according to an embodiment.

DETAILED DESCRIPTION

Figure 7:
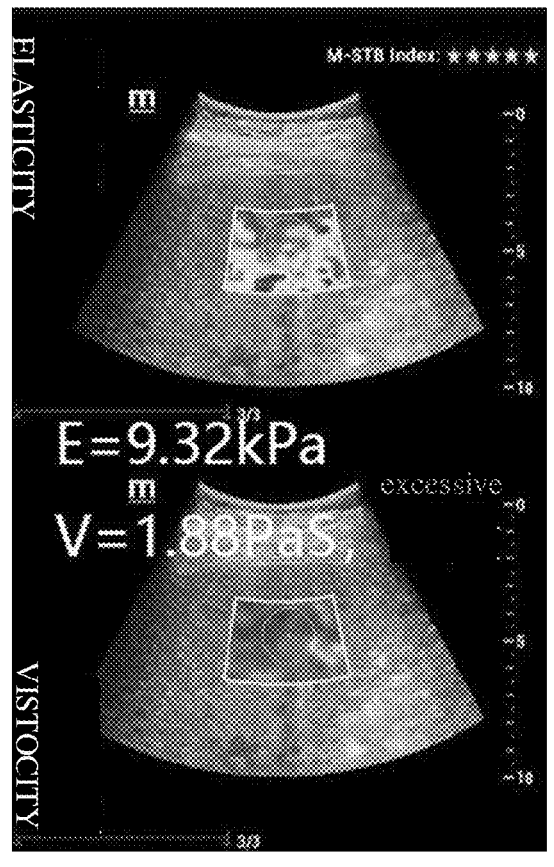
FIG. 7 is a schematic diagram of performing quality control on the elasticity result based at least on the viscosity parameter according to yet another embodiment.

The present disclosure will be further described in detail below through specific embodiments with reference to the accompanying drawings. Common or similar elements are referenced with like or identical reference numerals in different embodiments. Many details described in the following embodiments are for better understanding the present disclosure. However, those skilled in the art can realize with minimal effort that some of these features can be omitted in different cases or be replaced by other elements, materials and methods. For clarity some operations related to the present disclosure are not shown or illustrated herein so as to prevent the core from being overwhelmed by excessive descriptions. For those skilled in the art, such operations are not necessary to be explained in detail, and they can fully understand the related operations according to the description in the specification and the general technical knowledge in the art.

In addition, the features, operations or characteristics described in the specification may be combined in any suitable manner to form various embodiments. At the same time, the steps or actions in the described method can also be sequentially changed or adjusted in a manner that can be apparent to those skilled in the art. Therefore, the various sequences in the specification and the drawings are only for the purpose of describing a particular embodiment, and are not intended to be an order of necessity, unless otherwise stated one of the sequences must be followed.

The serial numbers of components herein, such as "first", "second", etc., are only used to distinguish the described objects and do not have any order or technical meaning. The terms "connected", "coupled" and the like here include direct and indirect connections (coupling) unless otherwise specified.

In some schemes, the following factors are taken into account for the quality control or evaluation of a result of elasticity imaging:

(1) too complex tissue structure, too large tissue depth or too strong tissue which may lead to problems of too small amplitude of shear waves generated, too fast attenuation when propagating, or complex propagation path, even difficult propagation, seriously affecting the quality of final shear wave imaging and the accuracy of elasticity measured results; and (2) amplitude of shear waves particularly prone to be affected by disturbances such as breathing, blood vessel pulsation and probe movement due to micrometer-scale amplitude of shear waves in tissues, leading to inaccurate elasticity result.

In view of the above factors, some schemes for evaluating the result of elasticity imaging have been also proposed. Even so, in most current studies about elasticity imaging, tissues are regarded as a pure elastic body, and based on the assumption of which, elasticity imaging is performed to obtain a corresponding imaging result, i.e. the elasticity result. Especially for the quantitative elasticity imaging technique, only elasticity modulus is calculated for display. However, a growing number of studies have shown that in addition to elasticity, human tissue also has the property of viscosity. Elasticity and viscosity jointly affect the propagation velocity of shear waves in tissues. Therefore, the inventors believe that when the viscosity of tissues is strong, even if there are no other adverse factors affecting elasticity imaging, the elasticity result calculated according to a model of the above-mentioned pure elastic body may still be inaccurate or unreliable; accordingly, there may exist mismatch between a measured elasticity result and an actual elasticity result of tissues, which may lead to errors and misdiagnoses. For example, the inventors found that: in clinical staging diagnosis of liver fibrosis using elasticity imaging, when AST/ALT is five times higher than normal value or in patients with acute hepatitis, the elasticity result measured may also be increased abnormally and may be inconsistent with actual liver fibrosis, which may possibly be caused by excessive tissue viscosity. Average doctors, especially inexperienced ones, are prone to overlook such special conditions during the use of elasticity imaging and make wrong diagnoses.

Based on the above considerations, the inventors conceive of performing quality control on the reliability of elasticity results with tissue viscosity.

The present disclosure may be applied to an ultrasonic imaging system. Referring to FIG. 1, the ultrasonic imaging system in some embodiments may include an ultrasonic probe 10, a transmitting and receiving control circuit 20, an echo processing unit 30, a processor 40 and a display 50. These components are described below.

The ultrasonic probe 10 may be used to transmit ultrasonic waves to a region of interest and receive echo signals of the ultrasonic waves. In some embodiments, the ultrasonic probe 10 may be a general one-dimensional probe, a matrix probe or a four-dimensional probe with mechanical device, which is not limited herein in this regard as long as the ultrasonic probe adopted can obtain the echo signals of the ultrasonic waves (or data) of a target region of a person being examined. In some specific embodiments, the ultrasonic probe 10 may include a plurality of array elements for conversion of electrical pulse signals and ultrasonic waves thereby performing the transmission of the ultrasonic waves to a biological tissue under examination 60 (a biological tissue of human or animal body) and the reception of ultrasonic echoes reflected from the tissue to obtain echo signals of the ultrasonic waves. The plurality of array elements included in the ultrasonic probe 10 may be arranged in a row to form a linear array, or in a two-dimensional matrix to form a plane array, or to form a convex array. The array elements may transmit ultrasonic waves according to excitation of electrical signals, or convert the received ultrasonic waves into electrical signals. Accordingly, each array element may be used to transmit ultrasonic waves to the region of interest of the biological tissue, or receive the echo signals of the ultrasonic waves returned from the tissue. When performing ultrasonic detection, a transmitting sequence and a receiving sequence may be used to control which array elements are used for transmitting ultrasonic waves and which array elements are used for receiving ultrasonic waves, or to control the array elements to transmit ultrasonic waves or receive ultrasonic echoes in a time-slot manner. All the array elements involved in transmission of the ultrasonic waves may be excited by electrical signals to simultaneously transmit the ultrasonic waves; alternatively, the array elements involved in transmission of the ultrasonic waves may be excited by several electrical signals with a certain time interval so as to continuously transmit the ultrasonic waves with a certain time interval.

In an example, the region of interest may be selected by users. For example, when a conventional ultrasonic image is displayed on the display 50, the region of interest may be selected on the conventional ultrasonic image. In another example, the position of the region of interest may be automatically determined by the processor 40 on a basic ultrasonic image based on an associated machine recognition algorithm. In yet another example, the region of interest may be obtained by semi-automatic detection. For example, the position of the region of interest may be automatically detected by the processor 40 on the basic ultrasonic image based on the machine recognition and then be modified or corrected by users to obtain a more accurate position of the region of interest.

The transmitting and receiving control circuit 20 may be used to control the ultrasonic probe 10 to perform the transmission of ultrasonic waves and the reception of the echo signals of the ultrasonic waves. Specifically, the transmitting and receiving control circuit 20 may be used to control the ultrasonic probe 10 transmit ultrasonic waves to the biological tissue such as the region of interest, and control the ultrasonic probe 10 to receive ultrasonic echoes of the ultrasonic waves returned by the tissue. In some embodiments, the transmitting and receiving control circuit 20 may be used to generate the transmitting sequence and the receiving sequence and output them to the ultrasonic probe 10. The transmitting sequence may be used to control part or all of the plurality of array elements in the ultrasonic probe 10 to transmit the ultrasonic waves to the biological tissue 60. Parameters of the transmitting sequence may include the number of array elements involved in transmission and transmitting parameters of the ultrasonic waves (such as amplitude, frequency, the number of waves transmitted, transmission interval, transmission angle, waveform and/or focus position). The receiving sequence may be used to control part or all of the plurality of array elements to receive echo waves of the ultrasonic waves from the tissue. Parameters of the receiving sequence may include the number of array elements involved in reception and receiving parameters of the echo waves (such as receiving angle, depth, etc.). The parameters of the transmitting sequence of the ultrasonic waves and the parameters of the receiving sequence of the echo waves may be different for different uses of the ultrasonic echo waves or different images generated based on the ultrasonic echo waves.

The echo processing unit 30 may be used to process the echo signals of the ultrasonic waves received by the ultrasonic probe 10, such as performing filtering, amplification, beamforming, etc. on the echo signals of the ultrasonic waves to obtain processed echo signals of the ultrasonic waves or data. In some embodiments, the echo processing unit 30 may output echo data of the ultrasonic waves to the processor 40. Alternatively, the echo data of the ultrasonic waves may be stored first in a memory and then be read out from the memory by the processor 40 when an operation based on the echo data of the ultrasonic waves is required. It should be appreciated by those skilled in the art that the echo processing unit 30 may be omitted when it is unnecessary to filter, amplify and beamform the echo signals of the ultrasonic waves in some embodiments.

The processor 40 may be used to obtain the echo signals of the ultrasonic waves or data and obtain required parameters or images by using a related algorithm. The processor 40 in some embodiments of the present disclosure may include but not limit to a central processing unit (CPU), a micro controller unit (MCU), a field-programmable gate array (FPGA) and digital signal processing (DSP) devices used to interpret computer instructions and process data in computer software. In some embodiments, the processor 40 may be configured to execute computer applications in non-transitory computer-readable storage medium to enable a sample analysis device to perform a corresponding detection procedure.

The display 50 may be used to display information, such as parameters and images obtained by the processor. It should be appreciated by those skilled in the art that the ultrasonic imaging system itself may not integrate a display unit, but instead may be coupled to a computer device (e.g. a computer) to display information via the display unit of the computer device in some embodiments.

Above are some descriptions of the ultrasonic imaging system. In some embodiments, with the ultrasonic imaging system, shear waves propagated in the region of interest may be detected to calculate the elasticity result and/or viscosity parameter of the region of interest.

There are various ways to generate shear waves in the region of interest. For example, the shear waves may be generated in the region of interest by external vibration. For another example, the shear waves may be generated in the region of interest by transmitting special pulses (such as acoustic radiation force impulses, ARFIs) to the region of interest by the ultrasonic probe 10. When the shear waves are generated in the region of interest by the acoustic radiation force impulses, the acoustic radiation force impulses may or may not be focused. Specifically, when the acoustic radiation force impulses are strongly focused, wave source generating the shear waves may be more focused; and when the acoustic radiation force impulses are weakly focused, the range of the shear waves generated is wider, and multiple shear-wave point sources may be approximated as propagating from multiple starting points in the range of shear waves generated. In addition, the range may also be widened directly by generating the shear waves at a plurality of different positions. Taking the acoustic radiation force impulses as an example, the propagation of the shear waves starting from the different positions may be generated by transmitting the acoustic radiation force impulses multiple times and focusing on different regions respectively. For example, FIG. 2(*a*) shows the shear waves generated by strong focusing, and FIG. 2(*b*) shows the propagation of the shear waves starting from the different positions generated by focusing on different regions. Of course, a larger range of shear waves can also be generated by external vibration, for example, by applying vibration at different positions from which the propagation of the shear waves can be generated.

In some embodiments of the present disclosure, the processor 40 may obtain the echo signals of the ultrasonic waves of the region of interest, wherein the shear waves are propagated in the region of interest, and the ultrasonic waves is used to detect the shear waves; further, the processor 40 may, according to the echo signals of the ultrasonic waves, calculate the elasticity result and the viscosity parameter of the region of interest, and perform quality control or evaluation on the elasticity result at least based on the viscosity parameter. The following is a specific description thereabout.

The region of interest involved above may be determined as follows.

The processor 40 may control the ultrasonic probe 10 via the transmitting and receiving control circuit 20 to transmit the first ultrasonic waves to the target tissue to obtain the echo signals of the first ultrasonic waves; the processor 40 may generate the ultrasonic image of the target tissue according to the echo signals of the first ultrasonic waves; the processor 40 may control the display 50 to display the ultrasonic image; and the processor 40 may obtain the region of interest on the ultrasonic image. For example, the region of interest may be selected in the ultrasonic image shown on the display 50 by a user via an input tool such as a mouse; or the region of interest may be automatically determined in the ultrasonic image shown on the display by the processor based on related machine recognition algorithms. For another example, the region of interest may be acquired by the processor through a semi-automatic detection way, such as automatically detect the position of the region of interest in the ultrasonic image shown on the display 50 firstly by the processor 40 based on a machine recognition algorithm and then modifying or correcting by the user via the input tool (e.g. the mouse) to obtain a more accurate position of the region of interest.

The ultrasonic image generated by the first ultrasonic waves mentioned above may be a B-mode image. By displaying the B-mode image, it is convenient for users to adjust the position of the ultrasonic probe to find a section and the region of interest for elasticity imaging or elasticity measurement.

After determining the region of interest, the shear waves may be generated within the region of interest. The way to generate the shear waves has been described above and will not be repeated here.

The processor 40 may, via the transmitting and receiving control circuit 20, control the ultrasonic probe 10 to transmit second ultrasonic waves which is used for detecting the shear waves in the region of interest to the region of interest to obtain echo signals of the second ultrasonic waves; and the processor 40 may calculate the elasticity result and/or the viscosity parameter of the region of interest according to the echo signals of the second ultrasonic waves.

In some examples, after the shear waves propagates within the region of interest, the ultrasonic waves may be continuously transmitted to the region of interest and echo signals or data may be received. By detecting and recording the propagation of the shear waves in the region of interest, the group velocity of the shear waves propagated may be calculated, and a phase velocity of shear waves propagated corresponding to one or more (e.g. at least two) frequencies may be calculated simultaneously. The elasticity result may be calculated according to the group velocity of the shear waves; and the viscosity parameter may be calculated according to the phase velocity of the shear waves. When there is viscosity in the tissues, the phase velocity of shear waves propagated corresponding to different frequencies may be different. Accordingly, the viscosity parameter of the tissues can be calculated by the phase velocity of shear wave with different frequencies reflecting the degree of viscosity of the tissues.

It can be seen that the present disclosure may be applied to all elasticity imaging techniques applicable to shear waves, including shear-wave elasticity imaging techniques based on acoustic radiation force and transient elasticity imaging techniques based on external vibrations, and the difference therebetween mainly lies in the way the shear waves are generated.

Taking the shear-wave elasticity imaging techniques based on acoustic radiation force as an example, for the transmitting sequence of elasticity imaging, it may first generally transmit a driving pulse to the vicinity of the tissue in the region of interest, and generate the shear waves propagated within the region of interest based on the effect of acoustic radiation force; then, for detecting and recording the propagation of the shear waves, a series of detection pulses such as the second ultrasonic waves referred to herein may be transmitted into the region of interest and ultrasonic echo waves may be received. Based on the echo signals (or data) at different moments, the propagation velocity of the shear waves may be calculated. The propagation velocity may generally be the group velocity, representing an overall propagation velocity of the shear waves. For an isotropic elastic tissue, there is a following relationship between the propagation velocity of the shear waves and the elasticity modulus of the tissue: Young's modulus $E=3\rho Cs^2$, shear modulus $G=\rho Cs^2$, where p is the density of the tissue, and Cs represents the propagation velocity of the shear waves (group velocity). Therefore, the elasticity result including Young's modulus and shear modulus may further be calculated based on the propagation velocity of the shear waves. In case of transient elasticity imaging, it is necessary to generate shear waves into the tissue through external vibrations, then transmit a series of detection pulses such as the second ultrasonic waves referred to herein into the region of interest, and receive ultrasonic echo waves, such that the propagation of the shear waves can be detected and recorded, and the elasticity result including elasticity modulus may finally be calculated.

In some embodiments, after receiving the detection pulses such as the echo signals of the second ultrasonic waves, the echo signals of the ultrasonic waves may be processed (calculating cross-correlation or autocorrelation among the echo signals at different moments) by the processor 40 to obtain tissue motion information during propagation of the shear waves (such as displacement, velocity, acceleration). The tissue is stationary or nearly stationary in general; and motion of the tissue occurs as the shear waves propagate through the tissue. When the propagation velocity of the shear waves is different, the shear waves propagated may arrive to different positions at the same moment. Accordingly, the propagation velocity of the shear waves may be deduced from the tissue motion information under different moments. Generally, the shear waves generated in practice may typically include multiple frequencies (or a range of frequencies, such as 50-200 Hz, or 100-600 Hz); and the group velocity obtained in elasticity calculation may refer to the overall propagation velocity of the shear waves containing multiple frequencies. The propagation velocity corresponding to shear waves of different frequencies is referred to as the phase velocity, which is different from the group velocity.

The elasticity result herein may be the elasticity parameter(s) and/or the elasticity image(s) (the elasticity distribution diagram). for example, the elasticity result here may be the elasticity parameter of each point within the region of interest, or the elasticity image generated by the elasticity parameter of each point within the region of interest (or the elasticity distribution diagram), where the value of each point in the image may represent the elasticity parameter of the point. The elasticity result herein may also be an average elasticity parameter calculated from the elasticity parameter of each point in the region of interest.

Sub-tissue motion information corresponding to the shear waves of corresponding frequency (e.g. one or more frequencies) may be obtained by filtering or spectrum analysis of the detected tissue motion information. Taking the acquisition of the phase velocities of shear waves of at least two frequencies as an example, for example the phase velocities V100 and V200 at 100 Hz and 200 Hz are calculated respectively; as shown in FIG. 3, due to the two different propagation velocities, the motion curves detected at the same position may be different. Of course, the two frequency points are an example, the amount of calculation thereof is small; and information about multiple frequency points may be extracted for more accurate estimation.

In some embodiments, when the tissue within the region of interest is a diffuse lesion, most parts of the tissue are relatively uniform (e.g. hepatic fibrosis); as shown in FIG. 4, after the source of the shear waves is generated, it is always propagated to both sides, and different phase velocities may be extracted from the left and right sides (e.g. 100 Hz from the left side and 200 Hz from the right side) to obtain two different phase velocities, then based on which the viscosity in the whole large region (in the rectangular box) may be calculated.

In some embodiments, the phase velocity is calculated for the purpose of quality control on the elasticity result; thus in some examples, without additional transmission and reception of the ultrasonic waves, only the phase velocity may be obtained by processing the echo signals that have been already obtained and are used for calculating the elasticity result, and subsequent quality control may be conducted. In other embodiments, additional transmission and reception of dedicated ultrasonic waves used for evaluation of quality control may also be added, which is similar to elasticity imaging sequence. However, in such cases where a separate sequence is required, it is generally necessary to simplify the detection process of the phase velocity of the shear waves as much as possible. For example, detection is only carried out at the boundary of the region of interest, and an average result in the region of interest may be calculated without paying attention to the differences among different regions inside, so as to reduce the number of transmissions and transmission time as far as possible.

Once the phase velocity is obtained, an estimate of the amount of tissue viscosity may be made. There are many ways to estimate the viscosity: for example, the difference or ratio of two fixed frequency points may be used directly as a viscosity estimation parameter. Theoretically, if the tissue viscosity is zero, the phase velocities corresponding to shear waves of different frequencies are exactly the same; and with the increase of viscosity, the phase velocity of shear waves with high frequency becomes larger. Therefore, for two fixed frequency points, the greater the difference in phase velocity therebetween, the greater the viscosity. For another example, the frequency dispersion slope value may also be used as the viscosity estimation parameter. The frequency dispersion slope is calculated by slope=(v2−v1)/(F2−F1), where F2 and F1 represent two different frequency values, and V2 and V1 represent the phase velocities corresponding to the above two frequencies. It can be seen that the greater the slope, the greater the difference therebetween. For yet another example, a viscous physical quantity viscosity or a viscosity may be calculated directly by using a corresponding viscoelasiticity fitting model; obviously, the greater the viscous physical quantity is, the higher the viscosity of the tissue is. For example, according to a Voigt model, there is a following relationship between the phase velocity of the shear waves CO and the viscosity:

$$c_\phi = \sqrt{\frac{2(\mu_1^2 + \omega^2 \mu_2^2)}{\rho\left(\mu_1 + \sqrt{\mu_1^2 + \omega^2 \mu_2^2}\right)}}$$

where $\rho$ is the density of the tissue, $\mu_1$ is the elasticity parameter of the shear waves of the tissue (also referred to as the shear elasticity), $\mu_2$ is the viscosity parameter of the shear waves of the tissue (also referred to as the shear viscosity), and w is the angular frequency of the current shear wave.

Therefore, in some embodiments, the processor 40 may calculate the viscosity parameter of the region of interest according to the echo signals of the second ultrasonic waves as follows: the processor 40 may obtain the phase velocities of shear waves of at least two frequencies according to the echo signals of the second ultrasonic waves; and the processor 40 may calculate the discrepancy in the phase velocities of shear waves of at least two frequencies as the viscosity parameter. In some embodiments, the discrepancy in the phase velocities of shear waves of at least two frequencies may include a difference or ratio of the abovementioned phase velocities of shear waves of at least two frequencies.

In some embodiments, the processor 40 may also calculate the viscosity parameter of the region of interest according to the echo signals of the second ultrasonic waves as follows: the processor 40 may obtain the phase velocities of shear waves of at least two frequencies according to the echo signals of the second ultrasonic waves; and the processor 40 may calculate the frequency dispersion slope value as the viscosity parameter according to the above-mentioned phase velocities of shear waves of at least two frequencies and corresponding frequencies.

In some embodiments, the processor 40 may also calculate the viscosity parameter of the region of interest according to the echo signals of the second ultrasonic waves as follows: the processor 40 may obtain the phase velocity of shear waves of at least one frequency according to the echo signals of the second ultrasonic waves; and the processor 40 may calculate viscosity as the viscosity parameter according to the phase velocity of shear waves of at least one frequency and corresponding frequency. For example, it is calculated according to the Voigt model above.

In some embodiments, the processor 40 may perform quality control on the elasticity result according to the phase velocities of shear waves of one or more (e.g. at least two) frequencies. For example, the viscosity parameter may be calculated based on the phase velocity firstly and the elasticity result may be performed by the processor 40 with quality control at least according to the viscosity parameter. In some embodiments, the processor 40 may also obtain the viscosity parameter by other ways and then perform quality control on the elasticity result at least according to the viscosity parameter.

For example, when the difference in phase velocity is large or the viscosity is too high, the result of quality control may show that the credibility decreases in the elasticity result; and when the difference in phase velocity is small or the viscosity is relatively low, the result of quality control may show that the credibility is good in the elasticity result.

Below is an explanation of how to perform quality control on the elasticity result.

In some embodiments, the processor 40 may perform quality control at least according to the viscosity parameter, which may include that: the processor 40 may compare the viscosity parameter with one or more thresholds to evaluate the credibility of the elasticity result and generate a corresponding prompt; and the processor 40 may control the display 50 to display the prompt.

After obtaining the viscosity parameter, it may be necessary to use the viscosity parameter to determine the quality control on the elasticity result. One or more thresholds may be preset in the ultrasonic imaging system, and then be compared with the viscosity parameter to evaluate the reliability of the elasticity result. The setting of the thresholds should be different depending on the calculation of the elasticity parameter. Taking the viscosity as the viscosity parameter as an example, when the viscosity parameter is the difference of the phase velocity or the frequency dispersion slope, a corresponding threshold may be set similarly.

The thresholds may generally be obtained statistically according to large samples of clinical data. By collecting a large number of clinical cases to obtain the elasticity result and the viscosity parameter, acquiring true disease results (such as the pathological analysis results of gold standard for diagnosis), and performing comparison to determine a range of the viscosity parameter where the elasticity result is significantly decreased in accuracy, an optimal threshold for the evaluation of quality control may be obtained. As mentioned above, there may be one or more thresholds. Assuming that there is a threshold Visco_thred, when the viscosity parameter Viscosity corresponding to the current elasticity measurement is greater than the threshold Visco_thred, the current elasticity result E is displayed as a symbol representing an invalid result such as "***" or "---", or the elasticity result E is displayed in a color representing an erroneous result such as red, or the evaluation of the quality control corresponding to the current elasticity result or the elasticity image may be additionally displayed as "unqualified", "suspicious" or "abnormal viscosity". these are just a few examples of how to evaluate the reliability of the elasticity result and to generate a corresponding prompt. For example, FIG. 5 is a specific example thereof, in which a B-mode image is displayed, as well as the region of interest selected on the B-mode image, the elasticity result E of the region of interest, and the evaluation of quality control as "unqualified".

As mentioned above, there is one or more thresholds, for example, two. Assuming that there are two thresholds, Visco_thred1 and Visco_thred2, and the threshold Visco_thred1 is less than the threshold Visco_thred2. When the viscosity parameter Viscosity is greater than the threshold Visco_thred2, it may indicate that the current elasticity result is invalid; when the viscosity parameter Viscosity is less than or equal to the threshold and greater than the threshold Visco_thred2, it may indicate that the current elasticity result is suspicious and the user may be warned to make multiple measurements or further confirmation in combination with other examination means (such as medical history, serological indicators, other imaging means such as MRI, pathological puncture results, etc.) so as to make a more accurate diagnosis for diseases; and when the viscosity parameter Viscosity is less than or equal to the threshold Visco_thred1, it may indicate that the current elasticity result is reliable or at least not affected by tissue viscosity.

In most cases, when the viscosity parameter is large, it may cause elasticity inaccuracy, so it is necessary to prompt the user; however, according to different clinical situations, the condition for the evaluation of quality control may also be different, including that the viscosity is too small or within a certain special range. For example, when the difference in phase velocity is calculated as a negative value, or the frequency dispersion slope is calculated as a negative value, the viscous result is very small, but it may also be an error caused by an error elastic echo signal or an excessive noise interference, and a prompt of quality control about abnormal measurement is also required.

In some embodiments, the processor 40 may perform quality control at least according to the viscosity parameter, which may include that: the processor 40 may generate a elasticity quality control score at least according to the viscosity parameter; and the processor 40 may control the display 50 to display the elasticity quality control score.

It may be quantified as an elasticity quality control score Quality according to the viscosity parameter Viscosity (such as a distribution between 0 and 100). The smaller the viscosity, the higher the score; and the higher the viscosity, the lower the score, giving the user a quantitative evaluation of quality control. In some examples, when the viscosity parameter Viscosity is greater than the threshold Visco_thred, the corresponding quality control score Quality may be marked as red, and green otherwise, so as to remind the user clearly. FIG. 6 is an example in which a B-mode image, a framed region of interest in the B-mode image, an elasticity result E of the region of interest, and "quality control score=50" are displayed and may be indicated as red.

In clinically elasticity imaging, instead of only acquiring one elasticity parameter, users often obtain the distribution image of tissue elasticity (namely, the elasticity distribution diagram); that is, the elasticity of the tissue at various positions within the region of interest may vary. Similarly, the viscosity parameter of tissues at various positions may also be different; under such case, the average viscosity parameter in the whole region of interest may also be calculated to perform overall quality control evaluation; and the viscosity parameter may also be calculated separately from each local position in the whole region of interest, with the distribution of the viscosity parameter, i.e. the viscosity parameter distribution map, which may also be referred to as an elasticity quality control distribution diagram herein, so as to further obtain the distribution of quality control, and to facilitate more precise local quality control evaluation.

Thus, in some embodiments, the processor 40 may perform quality control on the elasticity result at least according to the viscosity parameter, which may include that: the processor may generate an elasticity quality control distribution diagram at least according to the viscosity parameter; and the processor 40 may control the display 50 to display the elasticity quality control distribution diagram. The value of each point in the elasticity quality control distribution diagram is calculated from at least the viscosity parameter of that point.

FIG. 7 is an example, a selected position in a fan-shaped region in the upper figure thereof is the region of interest showing a corresponding elasticity distribution diagram, and a selected position in a fan-shaped region in the lower figure thereof is the region of interest (corresponding to the region of interest in the upper figure) showing the elasticity quality control distribution diagram. Also shown in FIG. 7 are the elasticity parameter E and the viscosity parameter V of the region of interest, together with a prompt that the viscosity parameter is too large.

Figure 8:
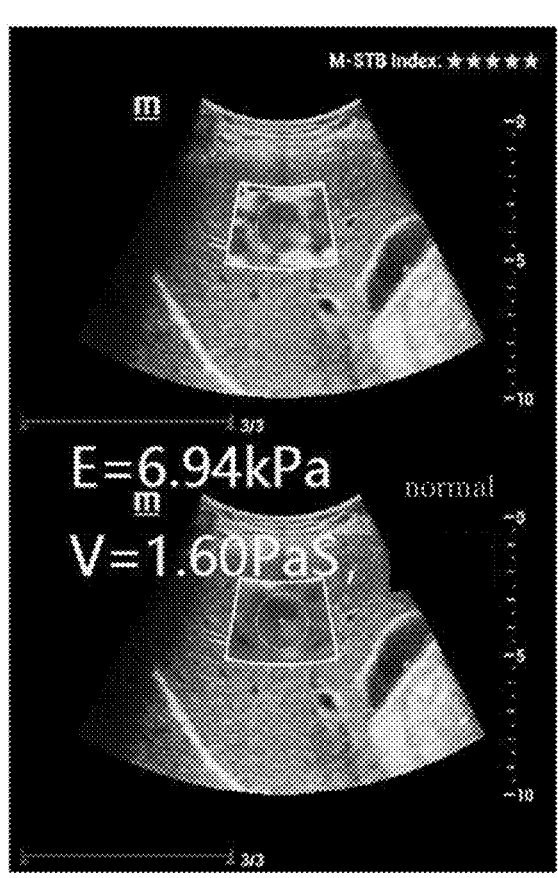
FIG. 8 is a schematic diagram of performing quality control on the elasticity result based at least on the viscosity parameter according to still another embodiment.

FIG. 8 is an example, a selected position in a fan-shaped region in the upper figure thereof is the region of interest showing a corresponding elasticity distribution diagram, and a selected position in a fan-shaped region in the lower figure thereof is the region of interest (corresponding to the region of interest in the upper figure) showing the elasticity quality control distribution diagram. Also shown in FIG. 8 are the elasticity parameter E and the viscosity parameter V of the region of interest, together with a prompt that the viscosity parameter is normal.

In some embodiments, the processor 40 may perform quality control on the elasticity result at least according to the viscosity parameter, which may include that: the processor 40 may empty a region in the elasticity distribution diagram where the quality control fails to meet the set requirements at least according to the viscosity parameter; wherein the elasticity distribution diagram is generated by the processor 40 according to the elasticity result.

In some examples, in shear-wave elasticity imaging techniques, shear wave propagation in tissue, which may be affected by various factors, such as insufficient acoustic energy, too large lesion, incapable propagation in liquid region and motion interference, may affect the reliability of the measured elasticity result, therefore shear-wave elasticity imaging techniques may also calculate a corresponding quality distribution diagram or quality score to perform quality control on the reliability of elasticity. In some embodiments of the present disclosure, it is critical to consider the effect of tissue viscosity on elasticity measurements. In some embodiments, the viscosity parameter may be weighted and averaged with an original quality parameter to obtain a comprehensive parameter result; or, the elasticity quality control score calculated by the viscosity parameter may be weighted and averaged with an original quality score (for example, it can be calculated by an original quality parameter) to obtain a comprehensive parameter result; or, the elasticity quality control image may be weighted averaged with the original quality distribution image (each point thereof calculated or characterized by the original quality parameter) to obtain an integrated image result. The elasticity result may be performed with quality control through above-mentioned comprehensive parameter result or the integrated image result.

Figure 9:
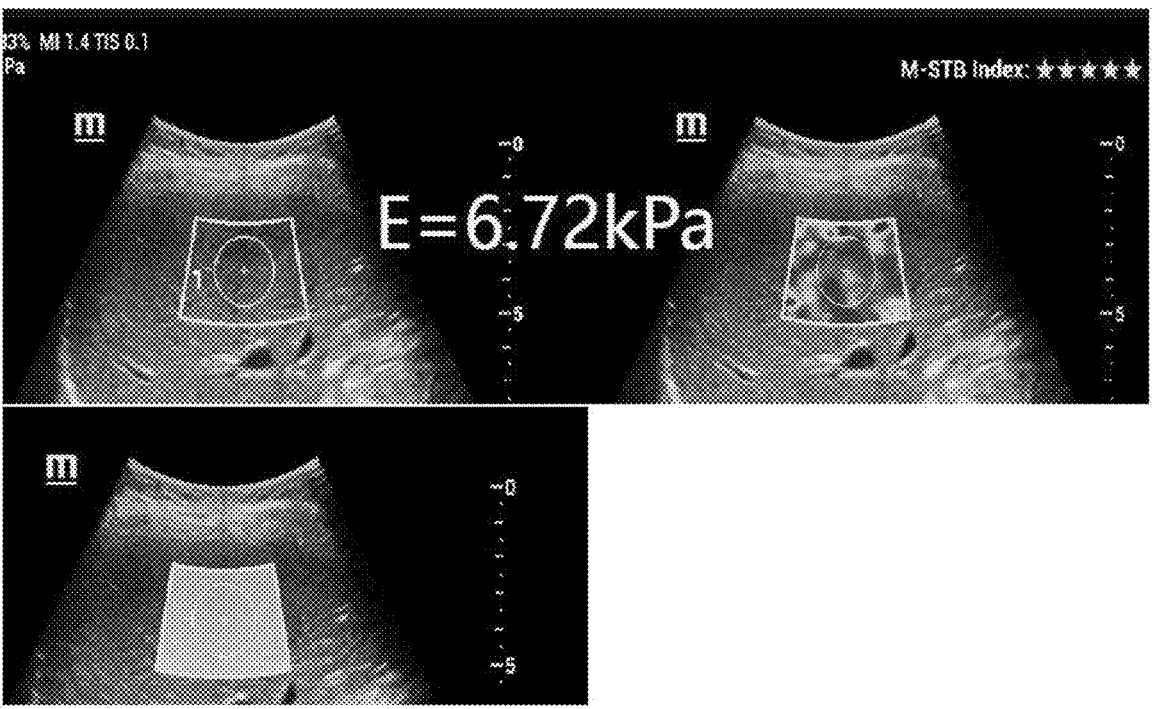
FIG. 9 is a schematic diagram of performing quality control on the elasticity result based at least on the viscosity parameter according to still yet another embodiment.

For example, suppose that the quality control score obtained by other original interference factors (insufficient acoustic energy, too large lesion, incapable propagation in liquid region and/or movement interference, etc.) is Q1, and the quality control score obtained by a viscous influencing factor herein is Q2, then a final quality control score $QF=Q1*a1+w2*(1-a1)$; where a1 is a weighting coefficient between 0 and 1. The smaller a1 is, the greater the influence of the viscosity on the quality control is. As shown in FIG. 9, in which the upper left image is a B-mode image, the upper right image is an elasticity image, and the lower left image is a comprehensive quality control image. In the comprehensive quality control image, green represents a reliable region, and purple represents an unreliable region. The user can select reliable regions in the image for elasticity result measurement, or decide whether to perform elasticity imaging again according to the distribution of green regions in the whole quality control image.

In one example, the previous quality parameters (i.e. considering the effects on elasticity result caused by other interference factors such as insufficient acoustic energy, excessive lesion size, non-transmission of fluid field and/or motion interference) may be calculated as follows: calculating an acceleration curve of each point in the region of interest according to the echo signals of the second ultrasonic waves, and calculating a flag value of each point according to the acceleration curve. The flag value is used for characterizing the degree of the point in the tissue being affected by interference; for example, the flag value characterizing the degree of the point in the tissue being affected by interference is the amplitude of the acceleration curve of the point which is the maximum value of the acceleration curve or the maximum value of the absolute value of the amplitude of the acceleration curve. The larger the amplitude of the acceleration curve is, the larger the shear stress is, and the less the influence of the disturbance is when encountering the interference. Accordingly, the amplitude of the acceleration curve can be used to characterize the degree being affected by influence. Then the credibility information about the region of interest (namely, the above-mentioned "original quality parameter") may be obtained according to the amplitude value of the acceleration curve at each point, for example, the magnitude of the acceleration curve of each point may be taken directly as the degree of credibility of the point (namely, the above-mentioned "original quality parameter"); or, the magnitude of the acceleration curve of each point may be normalized as the degree of credibility of the point; or, the magnitude of the acceleration curve of each point may be compared with a preset rule to determine the degree of credibility of the elasticity measured result of each point. For example, the degree of credibility may be divided into two levels, high and low, or may be divided into more levels. The credibility information about a target area is obtained according to the credibility of each mass point in the region of interest, and the credibility information about the target area may be a credibility distribution diagram (namely, the above-mentioned "original quality distribution image") of the target area, or may be a credibility ratio or a non-credibility ratio of the region of interest.

In some examples, due to a great difference between the viscosity characteristics of tissue and other factors affecting the signal-to-noise ratio of elasticity signal, other interference factors can be improved by adjusting probe section(s), increasing energy intensity, changing transmission frequency, avoiding blood vessels, repeated measurements for many times, and so one. However, viscosity abnormality is often related to some specific diseases or physiological intrinsic factors; so in actual clinical practice, doctors may be expected to have a clearer evaluation on the abnormality of the elasticity result caused by the interference of tissue viscosity. Thus, in some embodiments, an indication of quality control by viscosity may be added on the interface alone in the ultrasonic imaging system and displayed concurrently with the elasticity result (e.g. elasticity parameter or elasticity image). As shown in FIG. 10, the left image thereof is a B-mode image, and the right image thereof is an elasticity image of the selected region of interest. A prompt marker graph Visco Q index (for example, being an elasticity quality control image herein) for performing quality control by viscosity may be added on the interface, and an overall comprehensive viscosity parameter in the region of interest may be evaluated to provide a prompt according to the size thereof based on a plurality of levels preset in the system. For example, assuming that the degree of viscous interference is divided into five levels (i.e. level 1, level 2, . . . , level 5), each level corresponding to a viscous range, and a plurality of circles may be displayed correspondingly on the interface respectively to represent the degree of the viscous interference, then when the viscous interference is less than a certain level, the elasticity result would be hardly influenced and it is displayed in green at the same time; and when the viscous interference is greater than a certain level, the elasticity result would be influenced largely and it is displayed in red at the same time. Of course, displaying as circles is just an example, and other shapes (such as strip-shape, bulb-shape, pentagram-shape, etc.) may be adopted. Alternatively, it may also display a parameter value, such as 90% or 10%. At this point, the indication of quality control by viscosity represents an overall quality control by viscosity corresponding to the current frame of the elasticity result. Different frames correspond to different elasticity result, different elastic echo signals, and different indication of quality control by viscosity.

In some embodiments, the processor 40 may control the display 50 to display one or more of viscosity parameter, viscosity parameter distribution diagram, elasticity quality control distribution diagram, and elasticity quality control score in combination with any one or more of conventional B-mode images and elasticity images for users to comprehensively evaluate the quality of imaging.

A user operation sequence may be such that B-mode imaging detection is performed firstly, the ultrasonic probe may be adjusted to a suitable angle to obtain a suitable section by the user according to the position and morphology of the tissue observed in B-mode image in real time, the region of interest for elasticity detection may be determined, then the elasticity imaging process is started to transmit an ultrasonic elasticity scanning sequence and receive echo signals for calculation to obtain the elasticity result (parameter or image), and a prompt graph of quality control by viscosity (which may be referred to as a viscous quality control prompt graph) may be obtained at the same time and displayed synchronously with the elasticity image. The user can evaluate whether the current elasticity result is reliable according to the viscous quality control prompt graph.

A user operation sequence may be such that B-mode imaging detection is performed firstly, the ultrasonic probe may be adjusted to a suitable angle to obtain a suitable section by the user according to the position and morphology of the tissue observed in B-mode image in real time, the region of interest for elasticity detection may be determined, then the elasticity imaging process is started to transmit an ultrasonic elasticity scanning sequence and receive echo signals for calculation to obtain the elasticity result, and the elasticity quality control distribution diagram may be obtained at the same time and displayed synchronously with the elasticity image. The user can evaluate whether the current frame of the elasticity result or the elasticity measured result within the region of interest is reliable according to the elasticity quality control distribution diagram.

A user operation sequence may be such that B-mode imaging detection is performed firstly, the ultrasonic probe may be adjusted to a suitable angle to obtain a suitable section by the user according to the position and morphology of the tissue observed in B-mode image in real time, the region of interest for elasticity detection may be determined, then the elasticity imaging process is started to transmit an ultrasonic elasticity scanning sequence and receive echo signals for calculation to obtain the elasticity result, and an elasticity quality distribution diagram or an elasticity quality parameter may be obtained at the same time and displayed synchronously with the elasticity image. The user can evaluate whether the current frame of the elasticity result or the elasticity measured result within the region of interest is reliable according to the elasticity quality distribution diagram or the elasticity quality parameter. The elasticity quality distribution diagram or the elasticity quality parameter include the comprehensive influence of viscous interference, shear wave intensity and signal-to-noise ratio of echo signal.

An ultrasonic imaging method is also disclosed in some embodiments of the present disclosure, which is specifically described below.

Referring to FIG. 11, the ultrasonic imaging method in some embodiments may include the following steps:

Step 100: obtaining echo signals of the ultrasonic waves of the region of interest, wherein shear waves propagates within the region of interest, and the ultrasonic waves are used for detecting said shear waves.

The region of interest involved in step 100 above may be determined as follows:

In step 100, the ultrasonic probe 10 is controlled to transmit the first ultrasonic waves to the target tissue to acquire the echo signals of the first ultrasonic waves. In step 100, the ultrasonic image of target tissue is generated according to echo signals of the first ultrasonic waves. In step 100, the ultrasonic image is controlled to display. In step 100, the region of interest is acquired on the ultrasonic image. For example, a user can select the region of interest on the displayed ultrasonic image via an input tool such as a mouse, for another example, in step 100, the region of interest are automatically determined on the displayed ultrasonic image based on a relevant machine recognition algorithm; for yet another example, in step 100 the region of interest may also be acquired by means of semi-automatic detection. Specifically, in step 100, the position of the region of interest may be first automatically detected on the displayed ultrasonic image based on a machine recognition algorithm, and then is further modified or corrected by a user through an input tool such as a mouse so as to acquire a more accurate position of the region of interest.

The ultrasonic image formed by the first ultrasonic waves can be a B-mode image; and by displaying the B image, the user can easily adjust the position of the ultrasonic probe to find a section and region of interest of elasticity imaging or elasticity measurement.

After determining the region of interest, the shear waves may be generated within the region of interest in a manner that has been described above and will not be described in detail herein.

After determining the region of interest, in step 100, the ultrasonic probe is controlled to transmit the second ultrasonic waves to said region of interest to obtain the echo signals of the second ultrasonic waves. There is shear waves propagated in the region of interest, and the second ultrasonic waves is used to detect the shear waves in region of interest.

Step 110: calculating the elasticity result of the region of interest according to the echo signals of the ultrasonic waves.

For example, in step 110 the elasticity result of the region of interest may be calculated based on the echo signals of the second ultrasonic waves. Specific calculation procedures and principles may be referred to above and will not be described further herein.

Step 120: calculating the viscosity parameter of region of interest according to the echo signals of the ultrasonic waves.

In some embodiments, in step 120 the phase velocities of shear waves of at least two frequencies may be obtained from the ultrasonic waves, e.g. the echo signals of the second ultrasonic waves, and a discrepancy in the phase velocities of shear waves of at least two frequencies may be computed as the viscosity parameter. In some embodiments, the discrepancy in the phase velocities of shear waves of at least two frequencies may comprise a difference or ratio of the phase velocities of shear waves of at least two frequencies.

In some embodiments, in step 120, the phase velocities of shear waves of at least two frequencies may be obtained based on the ultrasonic waves, e.g. the echo signals of the second ultrasonic waves, and the frequency dispersion slope value may be computed as the viscosity parameter based on the phase velocities of shear waves of at least two frequencies and the corresponding frequencies.

In some embodiments, in step 120, the phase velocity of shear waves of at least one frequency may be obtained based on the ultrasonic waves, such as the echo signals of the second ultrasonic waves, and a viscosity may be calculated based on the phase velocity of shear waves of at least one frequency and a corresponding frequency as the viscosity parameter.

Step 130: performing quality control on the elasticity result at least according to the viscosity parameter.

In some embodiments, in step 130, the viscosity parameter may be compared to one or more thresholds to determine the reliability of the elasticity result and a corresponding prompt may be generated and displayed.

In some embodiments, in step 130, the elasticity quality control score may be generated at least according to the viscosity parameter and the elasticity quality control score may be displayed.

In some embodiments, in step 130, the elasticity quality control distribution diagram is generated based at least on the viscosity parameter and the elasticity quality control distribution diagram may be controlled for display.

In some embodiments, in step 130, a region of the elasticity distribution diagram where the quality control fails to meet a set requirement may be emptied based on at least the viscosity parameter; wherein the elasticity distribution diagram is generated according to the elasticity result, for example, elasticity parameters of various points.

The present disclosure is illustrated with reference to various exemplary embodiments. However, those skilled in the art may recognize that the exemplary embodiments can be changed and modified without departing from the scope of the present disclosure. For example, various operation steps and components used to execute the operation steps may be implemented in different ways (for example, one or more steps may be deleted, modified, or combined into other steps) according to specific application(s) or any number of cost functions associated with the operation of the system.

In addition, as understood by those skilled in the art, the principles herein may be reflected in a computer program product on a computer-readable storage medium that is preloaded with computer-readable program code. Any tangible, non-temporary computer-readable storage medium can be used, including magnetic storage devices (hard disks, floppy disks, etc.), optical storage devices (CD-ROMs, DVDs, Blu Ray disks, etc.), flash memory and/or the like. The computer program instructions may be loaded onto a general purpose computer, a special purpose computer, or other programmable data processing device to form a machine, so that these instructions executed on a computer or other programmable data processing device can form a device that realizes a specified function. These computer program instructions may also be stored in a computer-readable memory that can instruct a computer or other programmable data processing device to run in a specific way, so that the instructions stored in the computer-readable memory can form a manufacturing product, including a realization device to achieve a specified function. The computer program instructions may also be loaded onto a computer or other programmable data processing device to execute a series of operating steps on the computer or other programmable device to produce a computer-implemented process, so that instructions executed on the computer or other programmable device can provide steps for implementing a specified function.

Although the principles herein have been shown in various embodiments, many modifications to structures, arrangements, proportions, elements, materials, and components that are specifically adapted to specific environmental and operational requirements may be used without deviating from the principles and scope of the present disclosure. These and other modifications and amendments will be included in the scope of the present disclosure.

The foregoing specific description has been illustrated with reference to various embodiments. However, those skilled in the art will recognize that various modifications and changes can be made without departing from the scope of the present disclosure. Accordingly, the present disclosure is illustrative rather than restrictive, and all such modifications will be included in its scope. Similarly, there are solutions to these and other advantages and problems of the various embodiments as described above. However, the benefits, the advantages, solutions to problems, and any elements that can produce them or make them more explicit should not be interpreted as critical, required, or necessary one. The term "comprise" and any other variations thereof used herein are non-exclusive; accordingly, a process, method, article or device that includes a list of elements may include not only these elements, but also other elements that are not explicitly listed or are not part of said process, method, article or device. In addition, the term "coupling" and any other variations thereof as used herein may refer to physical, electrical, magnetic, optical, communication, functional, and/or any other connection.

Those skilled in the art will realize that many changes can be made to the details of the above embodiments without departing from the basic principles of the present disclosure. The scope of the present disclosure shall therefore be determined in accordance with the following claims.

The invention claimed is:

1. An ultrasonic imaging system, comprising:

an ultrasonic probe for transmitting ultrasonic waves to a target tissue and receiving echo signals of the ultrasonic waves of the target tissue;

a transmitting and receiving control circuit for controlling the ultrasonic probe to perform transmission of the ultrasonic waves and reception of the echo signals of the ultrasonic waves;

a processor and a display;

the processor being configured to:

control the ultrasonic probe via the transmitting and receiving control circuit to transmit first ultrasonic waves to the target tissue and receive echo signals of the first ultrasonic waves, and generate an ultrasonic image of the target tissue according to the echo signals of the first ultrasonic waves, control the display to display the ultrasonic image, and obtain a region of interest on the ultrasonic image;

control the ultrasonic probe via the transmitting and receiving control circuit to transmit second ultrasonic waves to the region of interest and receive echo signals of the second ultrasonic waves, wherein shear waves propagate in the region of interest, and the second ultrasonic waves are used for detecting the shear waves;

calculate an elasticity result and a viscosity parameter of the region of interest according to the echo signals of the second ultrasonic waves, the viscosity parameter comprising a viscosity of the region of interest, the elasticity result comprising an elasticity parameter or an elasticity image, and the elasticity parameter comprising Young's modulus or shear modulus; and perform quality control on the elasticity result at least according to the viscosity parameter, to generate, based on the viscosity parameter, a quality control result for indicating reliability of the elasticity parameter or the elasticity image, wherein, to perform the quality control on the elasticity result at least according to the viscosity parameter to generate, based on the viscosity parameter, the quality control result, the processor is further configured to:

compare the viscosity parameter with one or more thresholds to evaluate the reliability of the elasticity parameter or the elasticity image, to generate a prompt corresponding to the quality control result, and control the display to display the prompt; or generate an elasticity quality control score at least according to the viscosity parameter, wherein the elasticity quality control score increases as the viscosity parameter decreases, and control the display to display the elasticity quality control score; or generate an elasticity quality control distribution diagram at least according to the viscosity parameter, wherein the elasticity quality control distribution diagram comprises a viscosity parameter of each position in the region of interest, and control the display to display the elasticity quality control distribution diagram, wherein to calculate the viscosity parameter of the region of interest according to the echo signals of the second ultrasonic waves, the processor is further configured to:

obtain a phase velocity of shear waves of at least one frequency according to the echo signals of the second ultrasonic waves, and calculate the viscosity as the viscosity parameter according to the phase velocity of the shear waves of at least one frequency and the corresponding at least one frequency.

2. The ultrasonic imaging system according to claim 1, wherein to calculate the viscosity parameter of the region of interest according to the echo signals of the second ultrasonic waves, the processor is further configured to:

obtain phase velocities of shear waves of at least two frequencies according to the echo signals of the second ultrasonic waves; and calculate a discrepancy in the phase velocities of the shear waves of at least two frequencies as the viscosity parameter.

3. The ultrasonic imaging system according to claim 2, wherein the discrepancy in the phase velocities of the shear waves of at least two frequencies comprises a difference or a ratio of the phase velocities of the shear waves of at least two frequencies.

4. The ultrasonic imaging system according to claim 1, wherein to calculate the viscosity parameter of the region of interest according to the echo signals of the second ultrasonic waves, the processor is further configured to:

obtain phase velocities of shear waves of at least two frequencies according to the echo signals of the second ultrasonic waves; and calculate a frequency dispersion slope value as the viscosity parameter according to the phase velocities of the shear waves of at least two frequencies and the corresponding at least two frequencies.

5. An ultrasonic imaging system, comprising:

an ultrasonic probe for transmitting ultrasonic waves to a target tissue and receiving echo signals of the ultrasonic waves of the target tissue;

a transmitting and receiving control circuit for controlling the ultrasonic probe to perform transmission of the ultrasonic waves and reception of the echo signals of the ultrasonic waves;

a processor and a display;

the processor being configured to:

receive echo signals of the ultrasonic waves of a region of interest, wherein shear waves propagate in the region of interest, and the ultrasonic waves are used for detecting the shear waves;

calculate an elasticity result and a viscosity parameter of the region of interest according to the echo signals of the ultrasonic waves of the region of interest, the viscosity parameter comprising a viscosity of the region of interest, the elasticity result comprising an elasticity parameter or an elasticity image, and the elasticity parameter comprising Young's modulus or shear modulus; and perform quality control on the elasticity result at least according to the viscosity parameter, to generate, based on the viscosity parameter, a quality control result for indicating reliability of the elasticity parameter or the elasticity image, wherein to perform the quality control on the elasticity result at least according to the viscosity parameter to generate, based on the viscosity parameter, the quality control result, the processor is further configured to:

compare the viscosity parameter with one or more thresholds to evaluate the reliability of the elasticity parameter or the elasticity image, to generate a prompt corresponding to the quality control result, and control the display to display the prompt; or generate an elasticity quality control score at least according to the viscosity parameter, wherein the elasticity quality control score increases as the viscosity parameter decreases, and control the display to display the elasticity quality control score; or generate an elasticity quality control distribution diagram at least according to the viscosity parameter, wherein the elasticity quality control distribution diagram comprises a viscosity parameter of each position in the region of interest, and control the display to display the elasticity quality control distribution diagram, wherein to calculate the viscosity parameter of the region of interest according to the echo signals of the ultrasonic waves of the region of interest, the processor is further configured to:

obtain a phase velocity of shear waves of at least one frequency according to the echo signals of the ultrasonic waves of the region of interest, and calculate the viscosity as the viscosity parameter according to the phase velocity of the shear waves of at least one frequency and the corresponding at least one frequency.

6. The ultrasonic imaging system according to claim 5, wherein to calculate the viscosity parameter of the region of interest according to the echo signals of the ultrasonic waves of the region of interest, the processor is further configured to:

obtain phase velocities of shear waves of at least two frequencies according to the echo signals of the ultrasonic waves of the region of interest, and calculate a discrepancy in the phase velocities of the shear waves of at least two frequencies as the viscosity parameter; or obtain phase velocities of shear waves of at least two frequencies according to the echo signals of the ultrasonic waves of the region of interest, and calculate a frequency dispersion slope value as the viscosity parameter according to the phase velocities of the shear waves of at least two frequencies and the corresponding at least two frequencies.

7. An ultrasonic imaging method, performed by an ultrasonic imaging system comprising an ultrasonic probe, a transmitting and receiving control circuit, a processor, and a display, the ultrasonic imaging method comprising:

receiving, by the transmitting and receiving control circuit, echo signals of ultrasonic waves of a region of interest from a target tissue, wherein shear waves propagate in the region of interest, and the ultrasonic waves are used for detecting the shear waves;

calculating, by the processor, an elasticity result of the region of interest according to the echo signals of the ultrasonic waves, the elasticity result comprising an elasticity parameter or an elasticity image, and the elasticity parameter comprising Young's modulus or shear modulus;

calculating, by the processor, a viscosity parameter of the region of interest according to the echo signals of the ultrasonic waves, the viscosity parameter comprising a viscosity of the region of interest; and performing, by the processor, quality control on the elasticity result at least according to the viscosity parameter, to generate, based on the viscosity parameter, a quality control result for indicating reliability of the elasticity parameter or the elasticity image, wherein performing, by the processor, the quality control on the elasticity result at least according to the viscosity parameter to generate, based on the viscosity parameter, the quality control result comprises:

comparing the viscosity parameter with one or more thresholds to evaluate the reliability of the elasticity parameter or the elasticity image, to generate a prompt corresponding to the quality control result, and controlling the display to display the prompt; or generating an elasticity quality control score at least according to the viscosity parameter, wherein the elasticity quality control score increases as the viscosity parameter decreases, and controlling the display to display the elasticity quality control score; or generating an elasticity quality control distribution diagram at least according to the viscosity parameter, wherein the elasticity quality control distribution diagram comprises a viscosity parameter of each position in the region of interest, and controlling the display to display the elasticity quality control distribution diagram, wherein calculating, by the processor, the viscosity parameter of the region of interest according to the echo signals of the ultrasonic waves comprises:

obtaining a phase velocity of shear waves of at least one frequency according to the echo signals of the ultrasonic waves, and calculating the viscosity as the viscosity parameter according to the phase velocity of the shear waves of at least one frequency and the corresponding at least one frequency.

8. The ultrasonic imaging method according to claim 7, wherein calculating, by the processor, the viscosity parameter of the region of interest according to the echo signals of the ultrasonic waves further comprises:

obtaining phase velocities of shear waves of at least two frequencies according to the echo signals of the ultrasonic waves, and calculating a discrepancy in the phase velocities of the shear waves of at least two frequencies as the viscosity parameter; or obtaining phase velocities of shear waves of at least two frequencies according to the echo signals of the ultrasonic waves, and calculating a frequency dispersion slope value as the viscosity parameter according to the phase velocities of the shear waves of at least two frequencies and the corresponding at least two frequencies.

*    *    *    *    *